(12) United States Patent
Ye et al.

(10) Patent No.: US 10,391,104 B2
(45) Date of Patent: Aug. 27, 2019

(54) APPLICATION OF ANTIDEPRESSANT COMPOUND IN PREPARATION OF ANTIDEPRESSANT DRUGS AND ANTIDEPRESSANT HEALTH-CARE FOODS

(71) Applicant: ZHEJIANG ACADEMY OF MEDICAL SCIENCES, Hangzhou (CN)

(72) Inventors: Yiping Ye, Hangzhou (CN); Xiaoyu Li, Hangzhou (CN); Yewei Yang, Hangzhou (CN); Zhengrong Zhao, Hangzhou (CN); Fengyang Chen, Hangzhou (CN); Shifang Xu, Hangzhou (CN); Wenhai Huang, Hangzhou (CN)

(73) Assignee: ZHEJIANG ACADEMY OF MEDICAL SCIENCES, Zhejiang (CN)

( * ) Notice: Subject to any disclaimer, the term of this patent is extended or adjusted under 35 U.S.C. 154(b) by 0 days.

(21) Appl. No.: 15/579,608

(22) PCT Filed: Jun. 8, 2016

(86) PCT No.: PCT/CN2016/085265
§ 371 (c)(1),
(2) Date: Dec. 5, 2017

(87) PCT Pub. No.: WO2016/197944
PCT Pub. Date: Dec. 15, 2016

(65) Prior Publication Data
US 2018/0177801 A1    Jun. 28, 2018

(30) Foreign Application Priority Data

Jun. 12, 2015    (CN) .......................... 2015 1 0324854

(51) Int. Cl.
| | | |
|---|---|---|
| *A61K 31/569* | (2006.01) | |
| *A61P 25/24* | (2006.01) | |
| *A61K 9/00* | (2006.01) | |
| *A61K 9/20* | (2006.01) | |
| *A61K 9/48* | (2006.01) | |
| *A61K 9/08* | (2006.01) | |
| *A61K 9/14* | (2006.01) | |
| *A61K 31/58* | (2006.01) | |
| *A61K 45/06* | (2006.01) | |
| *A61K 36/24* | (2006.01) | |
| *A61K 36/27* | (2006.01) | |

(52) U.S. Cl.
CPC .......... *A61K 31/569* (2013.01); *A61K 9/0019* (2013.01); *A61K 9/0056* (2013.01); *A61K 9/0095* (2013.01); *A61K 9/08* (2013.01); *A61K 9/14* (2013.01); *A61K 9/20* (2013.01); *A61K 9/48* (2013.01); *A61K 31/58* (2013.01); *A61K 36/24* (2013.01); *A61K 36/27* (2013.01); *A61K 45/06* (2013.01); *A61P 25/24* (2018.01)

(58) Field of Classification Search
CPC ...... A61K 31/569; A61K 9/0019; A61K 9/20; A61P 25/24
See application file for complete search history.

(56) References Cited

FOREIGN PATENT DOCUMENTS

| CN | 1634097 A | | 7/2005 |
|---|---|---|---|
| CN | 104473946 | * | 4/2015 |
| CN | 104473946 A | | 4/2015 |
| CN | 104523724 | * | 4/2015 |

(Continued)

OTHER PUBLICATIONS

Chen et al., "Stephanthraniline A inhibits the proliferation and activation of T cells in vitro and in vivo." European J. of Pharmacology, vol. 685, pp. 186-197 (Year: 2012).*

(Continued)

*Primary Examiner* — Barbara P Badio
(74) *Attorney, Agent, or Firm* — Wood Herron & Evans LLP

(57) ABSTRACT

The present invention discloses an application of an antidepressant compound in preparation of antidepressant drugs and antidepressant health-care foods, where the antidepressant compound has a structure represented by formula I. The antidepressant compound serves as the only active ingredient or one of active ingredients of antidepressant health-care foods. The antidepressant drug is a liquid preparation, a solid preparation, a spray, an aerosol, or the like. The antidepressant compound according to the present invention is applied in preparation of antidepressant drugs and antidepressant health-care foods, and has a chemical structure different from those of existing antidepressant drugs. The anti-depressant compound has significant antidepressant activities without obvious toxic and side effects, contributes to large-scale promotion and use on the market, and has broad application prospects.

Formula I

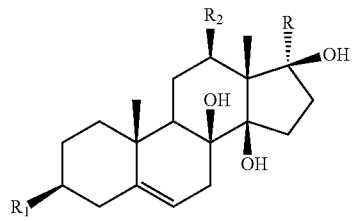

6 Claims, No Drawings

(56) References Cited

FOREIGN PATENT DOCUMENTS

| CN | 104523724 A | 4/2015 |
|---|---|---|
| CN | 104997788 A | 10/2015 |

OTHER PUBLICATIONS

Mitsuhashi et al., "Constituents of Asclepiadaceae plants. XI. Separation of new aglycons from Cynanchum caudatum." Chem. Pharm. Bull., 11(9), 1198-1200. Abstract only (Year: 1963).*

Mitsuhashi et al., "Struture of cynanchogenin and sarcostin." Steroids,2(3), 373-378. Abstract only (Year: 1963).*

Newman DJ et al., "Natural products as sources of new drugs over the 30 years from 1981 to 2010", J Nat Prod, 2012, p. 311-335, vol. 75; 25 pgs.

Mathew SJ et al., "Novel drugs and therapeutic targets for severe mood disorders", Neuropsychopharmacology, 2008, p. 1-13; 13 pgs.

Cryan JF et al., "A glutamate pathway to faster-acting antidepressants?", Science, 2010, p. 912-914, vol. 329; 3 pgs.

Berton O et al., "New approaches to antidepressant drug discovery: beyond monoamines", Neurosience, 2006, p. 137-151, vol. 7: 15 pgs.

Yang QX et al., "Cynanauriculoside C-E, three new antidepressant pregnane glycosides from Cynanchum auriculatum", Phytochemistry Letters, 2011, p. 170-175, vol. 4; 6 pgs.

Tsutomu Warashina et al., "Steroidal glycosides from Cynanchum caudatum", Phytochemistry, 1995, p. 199-204, vol. 39; 6 pgs.

Ye YP et al, "Immunomodulating Steroidal Glycosides from the Roots of Stephanotis mucronata", Helvetica Chimica Acta, 2004, p. 2378-2384, vol. 87; 7pgs.

Zhang RS et al., "Two new cytotoxic C-21 steroidal glycosides from the root of Cynanchum auriculatum", Tetrahedron, 2000, p. 3875-3879, vol. 56; 5 pgs.

Xiao-Xia MA et al., "New pregnane glycosides from the roots of Cynanchum otophyllum", Steroids, 2007, p. 778-786, vol. 72; 9 pgs.

Kazuko Yoshikawa et al., "Steroidal glycosides from the fresh stem of *Stephanotis lutchuensis* var. *japonica* (Asclepiadaceae). Chemical structures of stephanosides A-J", Chem Pharm Bull, 1996, p. 1790-1796, vol. 44; 7 pgs.

Fumiko Abe et al., "Pregnane glycosides from Marsdenia tomentosa", Chem Pharm Bull, 1999, p. 869-875, vol. 47; 7 pgs.

Sachiko Tsukamoto et al., "Studies on the constituents of Asclepiadaceae palnts. LX. Further studies on glycosides with a novel sugar chain containing a pair of optically isomeric sugars, D- and L-cymarose, from Cynanchum wilfordi", Chem Pharm Bull, 1985, p. 2294-2304, vol. 33; 11 pgs.

Tsutomu Warashina et al., "Steroidal glycosides from the root of Cynanchum caudatum M.", Chem Pharm Bull, 1995, p. 977-982, vol. 43; 6 pgs.

Xiaoyu Li et al., "Four new immunomodulating steroidal glycosides from the stems of Stephanotis mucronata", Steroids, 2016, p. 683-690, vol. 71; 8 pgs.

Xiujun Meng et al., "Research Progress of Novel Antidepressant Drugs", Chinese Journal of New Drugs, 2011, p. 1766-1774, vol. 20; 9 pgs with English abstract.

International Search Report dated Sep. 13, 2016 of corresponding International application No. PCT/CN2016/085265; 7 pgs.

* cited by examiner

APPLICATION OF ANTIDEPRESSANT COMPOUND IN PREPARATION OF ANTIDEPRESSANT DRUGS AND ANTIDEPRESSANT HEALTH-CARE FOODS

TECHNICAL FIELD

The present invention relates to the field of pharmaceutical technology, and in particular to an application of an antidepressant compound in preparation of antidepressant drugs and antidepressant health-care foods.

BACKGROUND

Depression is a high prevalence of mental disorders. At present, the traditional clinical antidepressant drugs are safe and efficacious mainly for cerebral monoamine neurotransmitters in patients with depression, but have main defects of: slow efficacy (taking weeks or even months to have an efficacy in smoothing symptoms), resistance to treatment (treatment-resistant depression) and relapse. Therefore, it is in urgent need of developing a fast-acting antidepressant drug for treatment-resistant depression in clinic.

According to the pathogenesis of depression, and around follow-up adaptive change of nervous system, such as neural plasticity, neurogenesis and hypothalamic-pituitary-adrenal (HPA) axis, now the targets of antidepressant drugs mainly include [Newman D J, Cragg G M. Natural products as sources of new drugs over the 30 years from 1981 to 2010. J Nat Prod, 2012, 75(3): 311-335.]: 1) acting on monoaminergic systems (biogenic amines for increasing neurotransmitters in brains of patients with depression: 5-hydroxytryptamine (5-HT); norepinephrine (NE), etc.), e.g. 5-HT selective serotonin reuptake inhibitors (SSRIs), NE serotonin-noradrenalin reuptake inhibitors (SNRIs) and dopamine modulators; 2) acting on glutamate receptors, e.g. NMDA receptor antagonists, AMPA receptor modulators; 3) acting on neuropeptide receptors, e.g. neurokinin (NK) receptor antagonists, corticotropin releasing hormone (CRH) receptor antagonists; 4) acting on glucocorticoid receptors (GR), e.g. glucocorticoid receptor antagonists. However, at present, the traditional clinical antidepressant drugs are safe and efficacious mainly for cerebral monoamine neurotransmitters in patients with depression, but have main defects of slow efficacy (taking weeks or even months to have an efficacy in slowing down symptoms), resistance to treatment (treatment-resistant depression) and relapse. Therefore, it is in urgent need of developing a fast-acting antidepressant drug for treatment-resistant depression in clinic [Mathew S J, Manji H K, Charney D S. Novel drugs and therapeutic targets for severe mood disorders. Neuropsychopharmacology 2008: 1-13. 2.] [Cryan J F, OLeary O F. A glutamate pathway to faster-acting antidepressants? Science 2010; 912-914.].

In recent years, the research on antidepressant drugs based on new mechanisms of non-monoaminergic biosystems (beyond monoaminergic systems) has attracted widespread attentions [Berton O, Nestler E J. New approaches to antidepressant drug discovery: beyond monoamines Neurosience 2006; 7:137-151]. Major pharmaceutical enterprises in the world have set off a wave of development of novel antidepressant drugs, and found a large number of novel compounds having antidepressant effects: melatonin receptor agonist agomelatine came into the European markets in 2009, and FDA approved the corticotropin releasing hormone receptor antagonist quetiapine as an antidepressant drug in 2009. Furthermore, many other drugs for treating major depressions, including amino acid neurotransmitter receptor antagonists (e.g., NMDA antagonists), neuropeptide antagonists (CRF-1, NK-1 antagonists), glucocorticoids receptor antagonists (GR antagonists), are approved by FDA in phase II and Ill clinical trials [Meng Xiujun, Qu Lei, Ma Yan et al, Research Progress of Novel Antidepressant Drugs. Chinese Journal of New Drugs 2011; 20: 1766-1774.].

$C_{21}$ steroids are widely distributed in the plant kingdom, and are especially most widely distributed in Asclepiadaceae plants. With pregnane or its isomers as the basic skeleton, $C_{21}$ steroids isolated from plants are present in plants mainly in the form of glycoside formed by aglycone and sugar, and glycoside may be hydrolyzed under acidic conditions to secondary glycoside or aglycone. The antidepression effect of plant-derived $C_{21}$ steroidal glycosides has been reported in literatures in recent years: Chinese patents provide applications of a few plant-derived $C_{21}$ steroidal glycosides (mixtures) in drugs for treatment and prevention of depression [Application of $C_{21}$ steroid glycoside in pharmacy CN 1634097A]; a literature reports three antidepressant $C_{21}$ steroidal glycosides isolated from *Cynanchum auriculatum* [Yang Q X, Ge Y C, Huang X Y, et. al., Cynanauriculoside C-E, three new antidepressant pregnane glycosides from *Cynanchum auriculatum*. Phytochemistry Letters 2011; 4:170-175.].

SUMMARY

The present invention provides an application of an antidepressant compound in preparation of antidepressant drugs and antidepressant health-care foods, and the chemical structure of the antidepressant compound is different from those of existing antidepressants.

An application of an antidepressant compound in preparation of antidepressant drugs and antidepressant health-care foods, where the antidepressant compound has a structure represented by formula I:

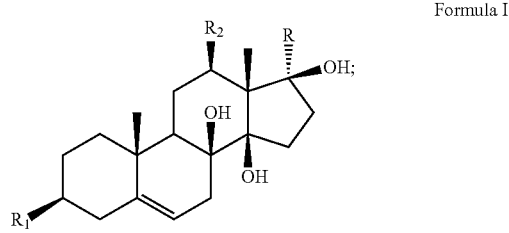

Formula I where a substituent $R_1$ is a hydroxyl group, sulfate or acetate;

a substituent $R_2$ is a hydroxyl group or an ester group; and a substituent R is an acetyl group or $CH_3CHR_3$, where a substituent $R_3$ in $CH_3CHR_3$ is a hydroxyl group or an ester group.

When the substituent $R_2$ is an ester group, the ester group therein may be one of the following groups: the ester group in the substituent $R_2$ is acetate, (Z)-2-methyl-2-butenoate, nicotinate, cinnamate, (N-methyl) anthranilate, benzoate, p-hydroxybenzoate or (2E)-3,4-dimethyl-2-en-pentanoate.

When the substituent $R_3$ is an ester group, the ester group therein may be one of the following groups: the ester group in the substituent $R_3$ is acetate, (Z)-2-methyl-2-butenoate, nicotinate, cinnamate, (N-methyl) anthranilate or benzoate.

The substituents and names of the above compounds are listed in Table 1.

TABLE 1

Sarcostin and its derivatives, deacetylmetaplexigenin and its derivatives

| SN | Name | $R_1$ | $R_2$ | R is $CH_3CHR_3$, where $R_3$ is |
|---|---|---|---|---|
| 1 | Sarcostin | Hydroxyl group | Hydroxyl group | Hydroxyl group |
| 2 | Stephanthroniline A | Hydroxyl group | Acetate | (N-methyl) anthranilate |
| 3 | 12-O-tigloyl-20-O-tigloyl-sarcostin | Hydroxyl group | (Z)-2-methyl-2-butenoate | (Z)-2-methyl-2-butenoate |
| 4 | 12-O-cinnamoyl-20-O-tigloylsarcostin | Hydroxyl group | Cinnamate | (Z)-2-methyl-2-butenoate |
| 5 | 12-O-tigloyl-20-O-cinnamoyl sarcostin | Hydroxyl group | (Z)-2-methyl-2-butenoate | Cinnamate |
| 6 | Kidjoladinin | Hydroxyl group | (Z)-2-methyl-2-butenoate | Acetate |
| 7 | Isokidjoladinin | Hydroxyl group | Acetate | (Z)-2-methyl-2-butenoate |
| 8 | Penupogenin | Hydroxyl group | Cinnamate | Hydroxyl group |
| 9 | Deacetylkidjoladinin | Hydroxyl group | (Z)-2-methyl-2-butenoate | Hydroxyl group |
| 10 | Isogagaminine | Hydroxyl group | Nicotinate | Cinnamate |
| 11 | Gagaminine | Hydroxyl group | Cinnamate | Nicotinate |
| 12 | 12-O-(N-methyl) anthraniloyl sarcostin | Hydroxyl group | (N-methyl) anthranilate | Hydroxyl group |
| 13 | 12-O-tigloyl-20-O-(N-methyl) anthraniloyl sarcostin | Hydroxyl group | (Z)-2-methyl-2-butenoate | (N-methyl) anthranilate |
| 14 | 12-O-benzoyl sarcostin | Hydroxyl group | Benzoate | Hydroxyl group |
| 15 | 12-O-nicotinoyl sarcostin | Hydroxyl group | Hydroxyl group | Nicotinate |
| 16 | 20-O-cinnamoyl sarcostin | Hydroxyl group | Hydroxyl group | Cinnamate |
| 17 | 12-O-cinnamoyl-20-O-ikemaoylsarcostin | Hydroxyl group | Cinnamate | (2E)-3,4-dimethyl-2-en-pentanoate |

| | Name | $R_1$ | $R_2$ | R |
|---|---|---|---|---|
| 18 | Deacetylmetaplexigenin | Hydroxyl group | Hydroxyl group | Acetyl group |
| 19 | Metaplexigenin | Hydroxyl group | Acetate | Acetyl group |
| 20 | Caudatin | Hydroxyl group | (2E)-3,4-dimethyl-2-en-pentanoate | Acetyl group |
| 21 | Qingyangshengenin | Hydroxyl group | p-hydroxybenzoate | Acetyl group |
| 22 | 12-O-cinnamoyldeacetyl metaplexigenin | Hydroxyl group | Cinnamate | Acetyl group |
| 23 | 12-O-(N-methyl) anthraniloyl deacetylmetaplexigenin | Hydroxyl group | (N-methyl) anthranilate | Acetyl group |
| 24 | 12-O-benzoyldeacetyl metaplexigenin | Hydroxyl group | Benzoate | Acetyl group |
| 25 | $R_1$ is sulfate, and others are identical to compounds 1-24, namely, 3-sulfate of compounds 1-24 | | | |
| 26 | $R_1$ is acetate, and others are identical to compounds 1-24, namely, 3-acetate of compounds 1-24 | | | |

For example, compound 1 is sarcostin: a substituent $R_1$=OH, a substituent $R_2$=OH, and a substituent R=$CH_3CHR_3$, where a substituent $R_3$=OH;

for another example, compound 18 is deacetylmetaplexigenin: a substituent $R_1$=OH, a substituent $R_2$=OH, and a substituent R=acetyl group ($CH_3CO$);

for another example, compound 19 is metaplexigenin: a substituent $R_1$=OH, a substituent $R_2$=acetate, and a substituent R=acetyl group ($CH_3CO$);

for another example, compound 20 is caudatin: a substituent $R_1$=OH, a substituent $R_2$=(2E)-3,4-dimethyl-2-en-pentanoate, and a substituent R=acetyl group ($CH_3CO$).

Preferably, the antidepressant compound is compound 3, compound 23, compound 25 or compound 26 in Table 1. In the antidepressant compound, the substituent $R_1$ is a hydroxyl group, sulfate or acetate; the substituent $R_2$ is (Z)-2-methyl-2-butenoate, the substituent R is $CH_3CHR_3$, and the substituent $R_3$ is (Z)-2-methyl-2-butenoate, or, the substituent $R_2$ is (N-methyl) anthranilate and the substituent R is an acetyl group ($CH_3CO$). The compound 3, compound 23 are novel compounds, and the sulfate or acetate derivatives corresponding to the compound 3 and compound 23 are also novel compounds.

The natural compound represented by general structural formula I according to the present invention, modified derivatives thereof and compositions of both may be used as active ingredients of pharmaceutical preparations or health-care foods, or as one of the active ingredients, and are prepared into various dosage forms, such as a liquid dosage form (injection, suspension, emulsion, solution, syrup, etc), a solid dosage form (tablet, capsule, granule, electuary, etc.), a spray, an aerosol, or the like by using accepted methods in the pharmaceutical field and food field. The pharmaceuticals of the present invention may be administrated via administration routes such as injection (intravenous injection, intravenous drip, intramuscular injection, intraperitoneal injection, subcutaneous injection), and oral administration, sublingual administration, mucosal dialysis, transdermal administration, or the like to treat depressions. That is, the antidepressant compound is used as the only active ingredient or one of the active ingredients of antidepressant drugs, and is used as the only active ingredient or one of the active ingredients of antidepressant health-care foods. The antidepressant drug is a liquid preparation, a solid preparation, a spray, an aerosol, or the like. The liquid preparation is an injection, a suspension, an emulsion, a solution, a syrup, or the like. The solid preparation is a tablet, a capsule, a granule, an electuary, or the like.

The natural compound (that is the antidepressant compound represented by structural formula I) according to the present invention refers to a compound that is extracted from plants, especially from *Stephanotis mucronata* (Blanco)

Merr., *Cynanchum bungei* Decne., and *Cynanchum Otophyllum* Schneid., and is represented by the above general formula of chemical structure. In particular, it is extracted from stems or roots of *Stephanotis mucronata* (Blanco) Merr., roots of *Cynanchum Bungei* Decne and roots of *Cynanchum Otophyllum* Schneid.

The extraction from plants in the present invention is a method that can be mastered and used by any staff in the field by dissolving and preparing the extract containing the compound represented by the above general formula of chemical structure from plants, especially from the stems or roots of *Stephanotis mucronata*, the roots of *Cynanchum Bungei* Decne. and the roots of *Cynanchum Otophyllum* Schneid. using short chain alcohols (methanol, ethanol) containing 1% to 90% water (volume percentage, similarly hereinafter), or acetone containing 1% to 90% water, or water saturated butanone, water saturated ethyl acetate, water saturated chloroform, water saturated dichloromethane or water saturated n-butanol at room temperature conditions (such as 0° C. to 30° C.), or under heating conditions (30° C. or above up to boiling temperature of solvent).

The compound represented by the above general formula of chemical structure (i.e., the anti-depressant compound represented by the structural formula I) according to the present invention refers to a naturally derived pregnane compound that is isolated and purified from the above extract using column chromatography (filler in the column is silicone, or octylated silicone, or octadecylated silicone, or sephadex) mastered and used by any staff in the field, and is identified by spectral analysis to determine its structure.

The chemical reaction and structural modification of the naturally derived pregnane compound according to the present invention refers to conventional chemical methods that can be mastered and used by any staff in the field, including a method of obtaining a polyoxygenated steroidal ester compound with a free hydroxyl group at C-3 or other sugar-binding sites through breaking the sugar chain of a pure naturally derived pregnane compound or mixtures thereof by weak acid hydrolysis; including a method of obtaining a derivative containing a plurality of hydroxyl groups by removing the original ester group through alkaline hydrolysis; and further including sulfating or acetifying the 3-hydroxyl group of the naturally derived pregnane compound.

When used as pharmaceuticals, the anti-depressant compound represented by the structural formula I according to the present invention may be directly used or used in the form of a pharmaceutical composition. That is, the antidepressant drug is a pharmaceutical composition containing 0.1 to 99% (wt), preferably 0.5 to 90% (wt), anti-depressant compound, the balance being pharmaceutically acceptable inert pharmaceutical carrier and/or excipient non-toxic to human and animals.

The pharmaceutical carrier or excipient is one or more solid, semi-solid and liquid diluents, fillers, and auxiliary agents for pharmaceutical products. The pharmaceutical compositions of the present invention are used in the form of unit body weight dosage. Compositions of Sarcostin and its derivatives thereof are prepared into various dosage forms, such as liquid dosage forms (injection, suspension, emulsion, solution, syrup, etc), solid dosage forms (tablet, capsule, granule, electuary, etc.), spray, aerosol, or the like by using accepted methods in the pharmaceutical field and food field. The pharmaceuticals of the present invention may be administrated via administration routes such as injection (intravenous injection, intravenous drip, intramuscular injection, intraperitoneal injection, subcutaneous injection), and oral administration, sublingual administration, mucosal dialysis, transdermal administration, or the like to treat depressions.

Compared with the prior art, the present invention has the following advantages:

The antidepressant compound according to the present invention is applied in preparation of antidepressant drugs and antidepressant health-care foods, and has a chemical structure different from those of existing antidepressant drugs. The anti-depressant compound has significant antidepressant activities without obvious toxic and side effects, contributes to large-scale promotion and use on the market, and has broad application prospects.

DETAILED DESCRIPTION

Embodiment 1: Preparation and Structural Identification of Sarcostin 5 kg of dried roots of *Cynanchum bungei* Decne. were ground, and percolated with a water solution of ethanol (water volume percentage: 5%), then the ethanol extract was obtained. The ethanol extract was extracted with ethyl acetate. The ethyl acetate extract was hydrolyzed with 0.2N methanol solution of sulfuric acid (that is, forming methanol solution of sulfuric acid by dissolving sulfuric acid in methanol, where sulfuric acid was at a concentration of 0.2 mol/L in the methanol solution of sulfuric acid) at 70° C. for 5 hours, neutralized with sodium bicarbonate, and concentrated. The concentrate was extracted with ethyl acetate, and the extract was total aglycone. Fr1 to Fr8 were obtained through silica gel column chromatography of 180 g of total aglycone with a dichloromethane-methanol system (volume ratio of dichloromethane to methanol: 100:0→40:60) by gradient elution. After repeated column chromatography with Rp-18 (reverse phase silicone), 15 g of Fr8 was eluted with a methanol-water system (volume percentage of methanol in the methanol-water system: 53%→60%), and identified with TLC (thin layer chromatography). Identical portions were combined, and recrystallized with methanol to obtain 2.3 g of sarcostin.

Sarcostin, $C_{21}H_{34}O_6$, colorless needles (methanol), melting point 151-153° C., and 254-257° C. (double melting points). ESI-MS (positive) m/z: 405.1 [M+Na]$^+$. $^{13}$C NMR ($C_5D_5N$, 125 MHz): 38.9 (C-1), 31.7 (C-2), 70.39 (C-3), 43.02 (C-4), 139.69 (C-5), 118.55 (C-6), 33.74 (C-7), 73.73 (C-8), 44.13 (C-9), 36.88 (C-10), 28.72 (C-11), 71.18 (C-12), 58.2 (C-13), 88.43 (C-14), 34.09 (C-15), 34.88 (C-16), 88.51 (C-17), 10.84 (C-18), 18.06 (C-19), 72.64 (C-20), 17.32 (C-21). $^1$H NMR ($C_5D_5N$, 500 MHz): δ 3.95 (1H, m, H-3), 5.45 (1H, br s, H-6), 3.97 (1H, m, H-12), 1.99 (3H, s, H-18), 1.49 (3H, s, H-19), 4.48 (1H, m, H-20), 1.54 (3H, d, J=6.0 Hz, H-21). This compound was identified as sarcostin, by comparison of its spectroscopic data, physical and chemical properties to those in the literature [Warashina T, Noro T. Steroidal glycosides from *Cynanchum caudatum*. Phytochemistry 1995; 39(1):199-204].

Embodiment 2: Preparation and Structural Identification of Deacetylmetaplexigenin 5 kg of dried roots of *Cynanchum bungei* Decne. were ground, and percolated with a water solution of ethanol (water volume percentage: 5%), then the ethanol extract was obtained. The ethanol extract was extracted with ethyl acetate. The ethyl acetate extract was hydrolyzed with 0.2N methanol solution of sulfuric acid at 70° C. for 5 hours, neutralized with sodium bicarbonate, and concentrated. The concentrate was extracted with ethyl acetate, and the extract was total aglycone. Fr1 to Fr8 were obtained through silica gel column chromatography of 180 g of total aglycone with a dichloromethane-methanol system (100:0→40:60) by gradient elution. After repeated Rp-18 column chromatography, 15 g of Fr8 was eluted with a methanol-water system (53%→60%), and identified with TLC. Identical portions were combined, and recrystallized with methanol to obtain 675 mg of deacetylmetaplexigenin.

Deacetylmetaplexigenin, $C_{21}H_{32}O_6$, colorless needles (methanol). IR (KBr): 3510, 1690 cm$^{-1}$. ESI-MS (positive) m/z: 403.1 [M+Na]$^+$. $^{13}$C NMR ($C_5D_5N$, 125 MHz): 39.0 (C-1), 31.9 (C-2), 71.4 (C-3), 43.2 (C-4), 140.1 (C-5), 118.6 (C-6), 34.0 (C-7), 74.2 (C-8), 44.8 (C-9), 37.2 (C-10), 29.3 (C-11), 68.8 (C-12), 60.2 (C-13), 89.2 (C-14), 34.9 (C-15), 32.6 (C-16), 92.4 (C-17), 9.2 (C-18), 18.3 (C-19), 209.4 (C-20), 27.7 (C-21). $^1$H NMR ($C_5D_5N$, 500 MHz): δ 3.93 (1H, m, H-3), 5.42 (1H, br s, H-6), 1.96 (3H, s, H-18), 1.49 (3H, s, H-19), 3.98 (1H, dd, J=11.5, 4.0 Hz, H-12), 2.68 (3H, s, H-21). This compound was identified as deacetylmetaplexigenin, by comparison of its spectroscopic data, physical and chemical properties to those in the literature [Ye Y P, Li X Y, Sun H X, Chen F Y, Pan Y J. Immunomodulating Steroidal Glycosides from the Roots of Stephanotis mucronata. Helvetica Chimica Acta 2004; 87:2378-2384].

Embodiment 3: Preparation and Structural Identification of Metaplexigenin 5 kg of dried roots of Cynanchum bungei Decne. were ground, and percolated with a water solution of ethanol (water volume percentage: 5%), then the ethanol extract was obtained. The ethanol extract was extracted with ethyl acetate. The ethyl acetate extract was hydrolyzed with 0.2N methanol solution of sulfuric acid at 70° C. for 5 hours, neutralized with sodium bicarbonate, and concentrated. The concentrate was extracted with ethyl acetate, and the extract was total aglycone. Fr1 to Fr8 were obtained through silica gel column chromatography of 180 g of total aglycone with a dichloromethane-methanol system (100:0→40:60) by gradient elution. After repeated Rp-18 column chromatography, 10 g of Fr6 was eluted with a methanol-water system (53%→60%), and identified with TLC. Identical portions were combined, and recrystallized with methanol to obtain 1.6 g of metaplexigenin.

Metaplexigenin, $C_{23}H_{34}O_7$, colorless needles (methanol). IR (KBr): 3510, 1690 cm$^{-1}$. ESI-MS (positive) m/z: 445.1 [M+Na]$^+$. $^{13}$C NMR ($C_5D_5N$, 125 MHz): 39.0 (C-1), 31.8 (C-2), 71.3 (C-3), 43.2 (C-4), 140.1 (C-5), 118.3 (C-6), 33.6 (C-7), 74.2 (C-8), 44.3 (C-9), 37.2 (C-10), 24.7 (C-11), 73.4 (C-12), 57.7 (C-13), 89.3 (C-14), 34.5 (C-15), 32.6 (C-16), 92.2 (C-17), 10.2 (C-18), 18.1 (C-19), 210.0 (C-20), 27.4 (C-21), 169.7 (C-1'), 20.6 (C-2'). $^1$H NMR ($C_5D_5N$, 500 MHz): δ 1.43 (3H, s, H-19), 2.51 (3H, s, H-21), 1.97 (3H, s, H-18), 5.00 (1H, dd, J=11.5, 4.0 Hz, H-12), 3.91 (1H, m, H-3), 5.35 (1H, br s, H-6), 2.10 (1H, s, H-2'). This compound was identified as metaplexigenin, by comparison of its spectroscopic data, physical and chemical properties to those in the literature [Ye Y P, Li X Y, Sun H X, Chen F Y, Pan Y J. Immunomodulating Steroidal Glycosides from the Roots of Stephanotis mucronata. Helvetica Chimica Acta 2004; 87:2378-2384].

Embodiment 4: Preparation and Structural Identification of Caudatin 5 kg of dried roots of Cynanchum bungei Decne. were ground, and percolated with a water solution of ethanol (water volume percentage: 5%), then the ethanol extract was obtained. The ethanol extract was extracted with ethyl acetate. The ethyl acetate extract was hydrolyzed with 0.2 N methanol solution of sulfuric acid at 70° C. for 5 hours, neutralized with sodium bicarbonate, and concentrated. The concentrate was extracted with ethyl acetate, and the extract was total aglycone. Fr1 to Fr8 were obtained through silica gel column chromatography of 180 g of total aglycone with a dichloromethane-methanol system (100:0→40:60) by gradient elution. After repeated Rp-18 column chromatography, 23 g of Fr3 was eluted with a methanol-water system (55%→60%), and identified with TLC. Identical portions were combined, and recrystallized with methanol-water to obtain 5.2 g of caudatin.

Caudatin, $C_{28}H_{42}O_7$, colorless slender prisms (methanol-water). ESI-MS (positive) m/z: 513.1 [M+Na]$^+$. $^{13}$C NMR (DMSOd$_6$, 125 MHz): 38.54 (C-1), 32.19 (C-2), 71.97 (C-3), 39.68 (C-4), 138.92 (C-5), 119.03 (C-6), 34.25 (C-7), 73.58 (C-8), 43.57 (C-9), 36.73 (C-10), 24.31 (C-11), 75.84 (C-12), 57.23 (C-13), 88.87 (C-14), 33.48 (C-15), 28.70 (C-16), 91.53 (C-17), 10.51 (C-18), 18.04 (C-19), 209.18 (C-20), 27.38 (C-21), 165.14 (C-1'), 113.59 (C-2'), 165.07 (C-3'), 37.61 (C-4'), 21.27 (C-5'), 21.08 (C-6'), 16.44 (C-7'). $^1$H NMR (DMSOd$_6$, 500 MHz): δ 3.88 (1H, m, H-3), 5.23 (1H, br s, H-6), 4.34 (1H, dd, J=11.5, 4.0 Hz, H-12), 2.04 (3H, s, H-18), 1.31 (3H, s, H-19), 2.50 (3H, s, H-21), 5.48 (1H, s, H-2'), 1.02 (3H, d, J=7.0 Hz, H-5'), 1.00 (3H, d, J=6.5 Hz, H-6'), 2.09 (3H, s, H-7'). This compound was identified as caudatin, by comparison with authentic sample on thin layer chromatography and high performance liquid chromatography, and also by comparison of its spectroscopic data to those in the literature [Zhang R S, Ye Y P, Shen Y M, Liang H L. Two new cytotoxic C-21 steroidal glycosides from the root of Cynanchum auriculatum Tetrahedron 2000, 56 (24): 3875-3879].

Embodiment 5: Preparation and Structural Identification of Qingyangshengenin 5 kg of dried roots of Cynanchum Otophyllum Schneid. were ground, and percolated with a water solution of ethanol (water volume percentage: 5%), then the ethanol extract was obtained. The ethanol extract was extracted with ethyl acetate. The ethyl acetate extract was hydrolyzed with 0.2N methanol solution of sulfuric acid at 70° C. for 5 hours, neutralized with sodium bicarbonate, and concentrated. The concentrate was extracted with ethyl acetate, and the extract was total aglycone. Fractions Fr1 to Fr3 were obtained through silica gel column chromatography of 165 g of total aglycone with a dichloromethane-methanol system (100:0→45:55) by gradient elution. After repeated Rp-18 column chromatography, 52 g of Fr2 was eluted with a methanol-water system to obtain 5.1 g of qingyangshengenin.

Qingyangshengenin, $C_{28}H_{36}O_8$, white amorphous powder. ESI-MS (positive) m/z: 523.1 [M+Na]$^+$. $^{13}$C NMR ($C_5D_5N$, 125 MHz): 39.51 (C-1), 32.31 (C-2), 71.92 (C-3), 43.56 (C-4), 140.65 (C-5), 118.82 (C-6), 35.16 (C-7), 74.76 (C-8), 44.84 (C-9), 37.72 (C-10), 25.53 (C-11), 73.74 (C-12), 58.75 (C-13), 89.91 (C-14), 33.51 (C-15), 34.24 (C-16), 92.83 (C-17), 11.18 (C-18), 18.67 (C-19), 210.17 (C-20), 28.13 (C-21), 15.73 (C-1'), 122.34 (C-2'), 132.75 (C-3', 7'), 116.52 (C-4', 6'), 163.91 (C-5'). $^1$H NMR ($C_5D_5N$, 500 MHz): δ 1.29 (3H, s, H-19), 2.01 (3H, s, H-18), 2.33 (3H, s, H-21), 3.74 (1H, m, H-3), 4.92 (1H, dd, J=11.5, 4.0 Hz, H-12), 5.26 (1H, br s, H-6), 7.14 (2H, d, H-4', 6'), 8.20 (2H, d, H-3', 7'). The compound was identified as qingyangshengenin, by comparison with authentic sample on thin layer chromatography and high performance liquid chromatography, and also by comparison of its spectroscopic data to those in the literature [Ma X X, Jiang F T, Yang Q X, Liu X H, Zhang Y J, Yang C R. New pregnane glycosides from the roots of *Cynanchum otophyllum*. Steroids 2007, 72: 778-786].

Embodiment 6: Preparation and Structural Identification of 12-O-acetyl-20-O—(N-methyl) Anthraniloyl Sarcostin 5 kg of dried stems of *Stephanotis mucronata* (Blanco) Merr. were ground, and percolated with a water solution of ethanol (water volume percentage: 5%), then the ethanol extract was obtained. The ethanol extract was extracted with ethyl acetate. The ethyl acetate extract was hydrolyzed with 0.2 N methanol solution of sulfuric acid at 70° C. for 5 hours, neutralized with sodium bicarbonate, and concentrated. The concentrate was extracted with ethyl acetate, and the extract was 192 g of total aglycone. 16.7 g of Fr1, 13.0 g of Fr2 and 14.5 g of Fr3 were obtained through silica gel column chromatography of 192 g of total aglycone with dichloromethane and dichloromethane-methanol systems by gradient elution. After column chromatography with Rp-18 (reverse phase silicone), 16.7 g of Fr1 was eluted with a methanol-water system (volume percentage of methanol in the methanol-water system: 50%→60%), and identified with TLC (thin layer chromatography). Identical portions were combined, and recrystallized with methanol to obtain 7.8 g of 12-O-acetyl-20-O—(N-methyl) anthraniloyl sarcostin.

12-O-acetyl-20-O—(N-methyl) anthraniloyl sarcostin, $C_{30}H_{42}NO_9$, colorless needles (methanol). HR-ESI-MS: 580.2871 ($[C_{31}H_{43}NO_8+Na]^+$; calculated value: 580.2886). $^{13}C$ NMR ($C_5D_5N$, 125 MHz): 38.6 (C-1), 30.8 (C-2), 71.8 (C-3), 41.9 (C-4), 139.7 (C-5), 118.2 (C-6), 34.3 (C-7), 74.1 (C-8), 43.1 (C-9), 36.7 (C-10), 24.7 (C-11), 73.5 (C-12), 56.0 (C-13), 87.8 (C-14), 32.2 (C-15), 32.9 (C-16), 87.8 (C-17), 10.3 (C-18), 18.2 (C-19), 73.9 (C-20), 15.0 (C-21), 171.4 (C-1'), 21.7 (C-2'), 109.6 (C-1'', 152.2 (C-2'', 110.9 (C-3'', 134.8 (C-4'', 114.4 (C-5''), 131.4 (C-6''), 167.2 (C-7''), 29.5 ($NCH_3$). $^1H$ NMR ($C_5D_5N$, 500 MHz): δ3.89 (1H, m, H-3), 5.38 (1H, br s, H-6), 5.25 (1H, dd, J=11.5, 3.5 Hz, H-12), 2.05 (3H, s, H-18), 5.20 (1H, q, J=6.5 Hz, H-20), 1.56 (1H, d, J=6.0 Hz, H-21), 2.13 (3H, s, H-2'), 6.75 (1H, d, J=8.5 Hz, H-3''), 7.42 (1H, ddd, J=8.5, 8.0, 1.5 Hz, H-4''), 6.60 (1H, t, J=7.0 Hz, H-5''), 8.37 (1H, dd, J=8.0, 2.0 Hz, H-6''), 2.81 (3H, d, J=5.0 Hz, NCH3). This compound was identified as 12-O-acetyl-20-O—(N-methyl) anthraniloyl sarcostin, by comparison of its spectroscopic data to those in the literature [Yoshikawa K, Okada N, Kann Y, Arihara S. Steroidal glycosides from the fresh stem of *Stephanotis lutchuensis* var. *japonica* (Asclepiadaceae). Chemical structures of stephanosides A-J. Chem Pharm Bull 1996; 44: 1790-1796].

Embodiment 7: Preparation and Structural Identification of Isokidjoladinin 5 kg of dried stems of *Stephanotis mucronata* (Blanco) Merr. were ground, and percolated with a water solution of ethanol (water volume percentage: 5%), then the ethanol extract was obtained. The ethanol extract was extracted with ethyl acetate. The ethyl acetate extract was hydrolyzed with 0.2 N methanol solution of sulfuric acid at 70° C. for 5 hours, neutralized with sodium bicarbonate, and concentrated. The concentrate was extracted with ethyl acetate, and the extract was 192 g of total aglycone. 16.7 g of Fr1, 13.0 g of Fr2 and 14.5 g of Fr3 were obtained through silica gel column chromatography of 192 g of total aglycone with dichloromethane and dichloromethane-methanol systems by gradient elution. After Rp-18 column chromatography, 16.7 g of Fr1 was eluted with a methanol-water system (50%→60%), and identified with TLC (thin layer chromatography). Identical portions were combined, and recrystallized with methanol to obtain 450 mg of isokidjoladinin.

Isokidjoladinin, $C_{28}H_{42}O_8$, colorless needles (methanol). ESI-MS (positive) m/z: 529.2 $[M+Na]^+$. $^{13}C$ NMR ($C_5D_5N$, 125 MHz): 38.9 (C-1), 32.0 (C-2), 71.5 (C-3), 43.2 (C-4), 139.7 (C-5), 118.6 (C-6), 34.7 (C-7), 74.1 (C-8), 43.9 (C-9), 37.3 (C-10), 25.6 (C-11), 74.5 (C-12), 56.7 (C-13), 88.8 (C-14), 33.6 (C-15), 33.4 (C-16), 87.5 (C-17), 10.9 (C-18), 18.1 (C-19), 74.8 (C-20), 15.1 (C-21), 171.2 (C-1'), 22.1 (C-2'), 167.0 (C-1'', 130.0 (C-2'', 136.9 (C-3''), 14.3 (C-4''), 12.5 (C-5''). $^1H$ NMR($C_5D_5N$, 500 MHz): δ1.32 (3H, s, H-19), 2.01 (3H, s, H-18), 1.47 (3H, s, H-21), 1.60 (3H, d, J=6.5 Hz, H-4''), 1.90 (3H, s, H-5''), 7.04 (1H, qd, J=6.0, 1.0 Hz, H-2''). This compound was identified as isokidjoladinin, by comparison of its spectroscopic data to those in the literature [Abe F, Okabe H, Yamauchi T, Honda K, Hayashi N. Pregnane glycosides from *Marsdenia tomentosa*. Chem Pharm Bull 1999; 47: 869-875].

Embodiment 8: Preparation and Structural Identification of Kidjoladinin 5 kg of dried stems of *Stephanotis mucronata* (Blanco) Merr. were ground, and percolated with a water solution of ethanol (water volume percentage: 5%), then the ethanol extract was obtained. The ethanol extract was extracted with ethyl acetate. The ethyl acetate extract was hydrolyzed with 0.2 N methanol solution of sulfuric acid at 70° C. for 5 hours, neutralized with sodium bicarbonate, and concentrated. The concentrate was extracted with ethyl acetate, and the extract was 192 g of total aglycone. 16.7 g of Fr1, 13.0 g of Fr2 and 14.5 g of Fr3 were obtained through silica gel column chromatography of 192 g of total aglycone with dichloromethane and dichloromethane-methanol systems by gradient elution. After Rp-18 column chromatography, 16.7 g of Fr1 was eluted with a methanol-water system (50%→60%), and identified with TLC (thin layer chromatography). Identical portions were combined, and recrystallized with methanol to obtain 210 mg of kidjolanine.

Kidjoladinin, $C_{28}H_{42}O_8$, colorless needles (methanol). ESI-MS (positive) m/z: 529.2 $[M+Na]^+$. $^{13}C$ NMR ($C_5D_5N$, 125 MHz): 39.3 (C-1), 32.3 (C-2), 71.8 (C-3), 43.6 (C-4), 140.4 (C-5), 118.9 (C-6), 35.1 (C-7), 74.6 (C-8), 44.3 (C-9), 37.4 (C-10), 25.5 (C-11), 75.2 (C-12), 56.6 (C-13), 89.0 (C-14), 33.7 (C-15), 34.0 (C-16), 87.9 (C-17), 11.4 (C-18), 18.5 (C-19), 74.8 (C-20), 15.7 (C-21), 167.5 (C-1') 129.7 (C-2'), 138.0 (C-3'), 14.7 (C-4'), 12.5 (C-5'), 171.6 (C-1''), 22.4 (C-2''). $^1H$ NMR($C_5D_5N$, 500 MHz): δ 3.90 (1H, m, H-3), 5.39 (1H, br s, H-6), 5.18 (1H, dd, J=11.5, 4.0, H-12), 2.24 (3H, s, H-18), 1.41 (3H, s, H-19), 5.08 (1H, q, J=6.5 Hz, H-20), 1.49 (3H, d, J=6.0 Hz, H-21), 6.56 (1H, d, J=7.5 Hz, H-3') 1.61 (3H, d, J=7.0 Hz, H-4'), 1.92 (3H, s, H-5'). 2.02 (1H, s, H-2''). This compound was identified as kidjoladinin, by comparison of its spectroscopic data to those in the literature [Tsukamoto S, Hayashi K, Mitsuhashi H. Studies on the constituents of Asclepiadaceae plants. LX. Further studies on glycosides with a novel sugar chain containing a pair of optically isomeric sugars, D- and L-cymarose, from *Cynanchum wilfordi*. Chem Pharm Bull 1985; 33:2294-2304.].

Embodiment 9: Preparation and Structural Identification of Deacetylkidjoladinin 5 kg of dried stems of *Stephanotis mucronata* (Blanco) Merr. were ground, and percolated with a water solution of ethanol (water volume percentage: 5%), then the ethanol extract was obtained. The ethanol extract was extracted with ethyl acetate. The ethyl acetate extract was hydrolyzed with 0.2 N methanol solution of sulfuric acid at 70° C. for 5 hours, neutralized with sodium bicarbonate, and concentrated. The concentrate was extracted with ethyl acetate, and the extract was 192 g of total aglycone. 16.7 g of Fr1, 13.0 g of Fr2 and 14.5 g of Fr3 were obtained through silica gel column chromatography of 192 g of total aglycone with dichloromethane and dichloromethane-methanol systems by gradient elution. 150 mg of deacetylkidjoladinin was obtained through Rp-18 column chromatography 13 g of Fr2, elution with a methanol-water system (50%→60%), and then through sephadex LH-20 column chromatography elution with methanol.

Deacetylkidjoladinin, $C_{26}H_{40}O_7$, white amorphous powder. El-MS (positive): m/z 487.3 $[M+Na]^+$. $^{13}C$ NMR ($C_5D_5N$, 125 MHz): 39.1 (C-1), 32.0 (C-2), 71.5 (C-3), 43.4 (C-4), 140.0 (C-5), 118.8 (C-6), 35.0 (C-7), 74.3 (C-8), 44.1 (C-9), 37.2 (C-10), 25.6 (C-11), 74.3 (C-12), 57.0 (C-13), 88.8 (C-14), 34.2 (C-15), 32.9 (C-16), 88.6 (C-17), 11.6 (C-18), 18.3 (C-19), 70.8 (C-20), 19.4 (C-21), 167.7 (C-1'), 129.7 (C-2'), 137.9 (C-3'), 14.2 (C-4'), 12.3 (C-5'). $^1H$ NMR ($C_5D_5N$, 500 MHz): δ 3.98 (1H, m, H-3), 5.34 (1H, m, H-6), 5.18 (1H, dd, J=11.0, 4.0 Hz, H-12), 2.06 (3H, s, H-18), 1.35 (3H, s, H-19), 4.42 (1H, m, H-20), 1.25 (3H, d, J=5.5 Hz, H-21), 7.28 (1H, dq, J=7.0, 1.0 Hz, H-3'), 1.51 (3H, dd, J=7.0, 1.0 Hz, H-4'), 1.96 (3H, s, H-5'). This compound was identified as deacetylkidjoladinin, by comparison of its spectroscopic data, physical and chemical properties to those in the literature [Abe F, Okabe H, Yamacuchi T, Honda K, Hayashi N. Pregnane glycosides from *Marsdenia tomenttosa* Chem Pharm Bull 1999; 47:869-875].

Embodiment 10: Preparation and Structural Identification of Penupogenin 5 kg of dried stems of *Stephanotis mucronata* (Blanco) Merr. were ground, and percolated with a water solution of ethanol (water volume percentage: 5%), then the ethanol extract was obtained. The ethanol extract was extracted with ethyl acetate. The ethyl acetate extract was hydrolyzed with 0.2 N methanol solution of sulfuric acid at 70° C. for 5 hours, neutralized with sodium bicarbonate, and concentrated. The concentrate was extracted with ethyl acetate, and the extract was 192 g of total aglycone. 16.7 g of Fr1, 13.0 g of Fr2 and 14.5 g of Fr3 were obtained through silica gel column chromatography of 192 g of total aglycone with dichloromethane and dichloromethane-methanol systems by gradient elution. After Rp-18 column chromatography, 13.0 g of Fr2 was eluted with a methanol-water system (50%→60%), and identified with TLC. Identical portions were combined, and recrystallized with methanol to obtain 130 mg of penupogenin.

Penupogenin, $C_{30}H_{40}O_7$, amorphous powder. El-MS (positive): m/z 535.3 $[M+Na]^+$. $^{13}C$ NMR($C_5D_5N$, 125 MHz): 39.1 (C-1), 32.0 (C-2), 71.6 (C-3), 43.4 (C-4), 140.0 (C-5), 118.9 (C-6), 35.0 (C-7), 74.2 (C-8), 44.2 (C-9), 37.2 (C-10), 25.7 (C-11), 74.8 (C-12), 56.9 (C-13), 88.8 (C-14), 34.2 (C-15), 32.9 (C-16), 88.6 (C-17), 11.7 (C-18), 18.3 (C-19), 70.9 (C-20), 19.3 (C-21), 165.9 (C-1'), 119.6 (C-2'), 145.2 (C-3'), 135.0 (C-4'), 128.6 (C-5', C-9'), 129.1 (C-6', C-8'), 130.5 (C-7'). $^1H$ NMR ($C_5D_5N$, 500 MHz): δ 1.38 (3H, s, H-19), 1.92 (3H, s, H-18), 2.13 (3H, s, H-21), 3.85 (1H, m, H-3), 4.41 (1H, m, H-20), 5.27 (1H, dd, J=11.5, 4.5 Hz, H-12), 5.36 (1H, br s, H-6), 6.93 (1H, d, J=16.0 Hz, H-2'), 7.50 (2H, d, J=6.5 Hz, H-5', 9'), 7.22 (2H, m, H-6', 8'), 7.24 (1H, m, H-7'), 8.14 (1H, d, J=16.0 Hz, H-3'). This compound was identified as penupogenin, by comparison of its spectroscopic data, physical and chemical properties to those in the literature [Warashina T, Noro T. Steroidal glycosides from the root of *Cynanchum caudatum* M. Chem Pharm Bull 1995; 43: 977-982].

Embodiment 11: Preparation and Structural Identification of Gagaminine 5 kg of dried stems of *Stephanotis mucronata* (Blanco) Merr. (5 kg) were ground, and percolated with a water solution of ethanol (water volume percentage: 5%), then the ethanol extract was obtained. The ethanol extract was extracted with ethyl acetate. The ethyl acetate extract was hydrolyzed with 0.2 N methanol solution of sulfuric acid at 70° C. for 5 hours, neutralized with sodium bicarbonate, and concentrated. The concentrate was extracted with ethyl acetate, and the extract was 192 g of total aglycone. 16.7 g of Fr1, 13.0 g of Fr2 and 14.5 g of Fr3 were obtained through silica gel column chromatography of 192 g of total aglycone with dichloromethane and dichloromethane-methanol systems by gradient elution. After Rp-18 column chromatography, 16.7 g of Fr1 was eluted with a methanol-water system (50%→60%), and identified with TLC. Identical portions were combined to obtain 320 mg of gagaminine.

Gagaminine, $C_{36}H_{43}NO_8$, amorphous powder, EI-MS (positive): m/z 618.3 $[M+H]^+$. $^{13}C$ NMR($C_5D_5N$, 125 MHz): 39.1 (C-1), 32.0 (C-2), 71.6 (C-3), 43.3 (C-4), 140.3 (C-5), 118.7 (C-6), 34.9 (C-7), 74.4 (C-8), 44.1 (C-9), 37.3 (C-10), 25.8 (C-11), 76.5 (C-12), 57.2 (C-13), 87.5 (C-14), 34.1 (C-15), 33.7 (C-16), 89.0 (C-17), 11.5 (C-18), 18.2 (C-19), 74.7 (C-20), 15.4 (C-21), 166.8 (C-1'), 120.3 (C-2'), 144.1 (C-3'), 136.0 (C-4'), 129.3 (C-5', C-9'), 128.6 (C-6', C-8'), 130.6 (C-7'), 151.4 (C-1"), 127.0 (C-2"), 137.5 (C-3"), 123.8 (C-4"), 153.8 (C-5"), 164.8 (C-6"). $^1H$ NMR ($C_5D_5N$, 500 MHz): δ 1.35 (3H, s, H-19), 1.56 (3H, d, J=6.0 Hz, H-21), 2.11 (3H, s, H-21), 3.87 (1H, m, H-3), 5.31 (1H, dd, J=11.0, 4.0 Hz, H-12), 5.36 (1H, br s, H-6), 6.54 (1H, d, J=16.0 Hz, H-2'), 7.35 (2H, m, H-6', 8'), 7.36 (1H, m, H-7'), 7.42 (2H, d, J=5.5 Hz, H-5', 9'), 7.84 (1H, d, J=16.0 Hz, H-3'), 7.21 (1H, dd, J=7.5, 4.5 Hz, H-5"), 8.32 (1H, br d, J=7.5 Hz, H-4"), 8.83 (1H, br d, J=4.5 Hz, H-6"), 9.52 (1H, s, H-2"). This compound was identified as gagaminine, by comparison of its spectroscopic data, physical and chemical properties to those in the literature [Tsukamoto S, Hayashi K, Mitsuhashi H. Studies on the constituents of Asclepiadaceae plants. LX. Further studies on glycosides with a novel sugar chain containing a pair of optically isomeric sugars, D- and L-cymarose, from *Cynanchum wilfordi*. Chem Pharm Bull 1985; 33: 2294-2304.].

Embodiment 12: Preparation and Structural Identification of Kidjoranine 5 kg of dried stems of *Stephanotis mucronata* (Blanco) Merr. were ground, and percolated with a water solution of ethanol (water volume percentage: 5%), then the ethanol extract was obtained. The ethanol extract was extracted with ethyl acetate. The ethyl acetate extract was hydrolyzed with 0.2 N methanol solution of sulfuric acid at 70° C. for 5 hours, neutralized with sodium bicarbonate, and concentrated. The concentrate was extracted with ethyl acetate, and the extract was 192 g of total aglycone. 16.7 g of Fr1, 13.0 g of Fr2 and 14.5 g of Fr3 were obtained through silica gel column chromatography of 192 g of total aglycone with dichloromethane and dichloromethane-methanol systems by gradient elution. After Rp-18 column chromatography, 13 g of Fr2 was eluted with a methanol-water system (50%→60%), and identified with TLC. Identical portions were combined, and 480 mg of kidjoranine was obtained through HPLC and Sephadex LH-20 column chromatography.

Kidjoranine, $C_{30}H_{38}O_7$, amorphous powder. EI-MS (positive): m/z 533.3 [M+Na]$^+$. $^{13}$C NMR($C_5D_5N$, 125 MHz): 39.1 (C-1), 32.0 (C-2), 70.5 (C-3), 43.3 (C-4), 140.3 (C-5), 118.4 (C-6), 34.7 (C-7), 74.3 (C-8), 44.5 (C-9), 37.3 (C-10), 25.0 (C-11), 73.6 (C-12), 58.1 (C-13), 92.4 (C-14), 34.0 (C-15), 33.0 (C-16), 89.5 (C-17), 10.6 (C-18), 18.3 (C-19), 209.8 (C-20), 27.6 (C-21), 165.8 (C-1'), 120.0 (C-2'), 144.9 (C-3'), 135.0 (C-4'), 128.5 (C-5', C-9'), 129.3 (C-6', C-8'), 130.5 (C-7'). $^1$H NMR ($C_5D_5N$, 500 MHz): δ 1.45 (3H, s, H-19), 2.08 (3H, s, H-18), 2.53 (3H, s, H-21), 3.92 (1H, m, H-3), 5.25 (1H, dd, J=11.5, 3.5 Hz, H-12), 5.37 (1H, br s, H-6), 6.87 (1H, d, J=16.0 Hz, H-2'), 7.37 (2H, m, H-6', 8'), 7.38 (1H, m, H-7'), 7.67 (2H, d, J=5.5 Hz, H-5', 9'), 8.05 (1H, d, J=16.0 Hz, H-3'). This compound was identified as kidjoranine, by comparison of its spectroscopic data, physical and chemical properties to those in the literature [Tsukamoto S, Hayashi K, Mitsuhashi H. Studies on the constituents of Asclepiadaceae plants. LX. Further studies on glycosides with a novel sugar chain containing a pair of optically isomeric sugars, D- and L-cymarose, from *Cynanchum wilfordi*. Chem Pharm Bull 1985; 33: 2294-2304.].

Embodiment 13: Preparation and Structural Identification of 12-O-tigloyl-20-O-tigloylsarcostin 5 kg of dried stems of *Stephanotis mucronata* (Blanco) Merr. were ground, and percolated with a water solution of ethanol (water volume percentage: 5%), then the ethanol extract was obtained. The ethanol extract was extracted with ethyl acetate. The ethyl acetate extract was hydrolyzed with 0.2 N methanol solution of sulfuric acid at 70° C. for 5 hours, neutralized with sodium bicarbonate, and concentrated. The concentrate was extracted with ethyl acetate, and the extract was 192 g of total aglycone. 16.7 g of Fr1, 13.0 g of Fr2 and 14.5 g of Fr3 were obtained through silica gel column chromatography of 192 g of total aglycone with dichloromethane and dichloromethane-methanol systems by gradient elution. After column chromatography with Rp-18 (reverse phase silicone), 13 g of Fr2 was eluted with a methanol-water system (volume percentage of methanol in the methanol-water system: 50%→60%), and identified with TLC (thin layer chromatography). Identical portions were combined, and 51 mg of compound 3 was obtained through HPLC and sephadex LH-20.

As indicated by structural identification, compound 3 is white amorphous powder positive to Liebermann-Burchard reaction, showing that there is a steroid nucleus structure in its molecule. The molecular formula was determined to be $C_{31}H_{46}O_8$ based on NMR and HRESI-MS data (m/z 547.3273 [M+H]$^+$, calcd. 547.3271). The $^{13}$C NMR and DEPT spectra (125 MHz, $C_5D_5N$) showed that compound 3 contains 31 carbon atoms, including 7 $CH_3$, 7 $CH_2$, 7 CH and 10 quaternary carbons. NMR spectral data of the steroid nucleus of compound 3 are similar to those of sarcostin provided in the literature [Li X Y, Sun H X, Ye Y P, Chen F Y, Tu J, Pan Y J. Four new immunomodulating steroidal glycosides from the stems of *Stephanotis mucronata*. Steroids, 2006, 71:683-690.], except that the $^{13}$C NMR, DEPT and $^1$H NMR spectra of compound 3 show the following data: (1) $^{13}$C signals at $δ_C$ 167.75 (s), 130.63 (s), 136.81 (d), 14.22 (q), 12.34 (q), $^1$H signals at $δ_H$ 6.88 (dq, J=7.0, 1.0 Hz), 1.65 (dd, J=7.0, 1.0 Hz), 2.02 (s); (2) $^{13}$C signals at $δ_C$ 166.60 (s), 129.57 (s), 135.89 (d), 14.03 (q), 12.12 (q), $^1$H signals at $δ_H$ 6.80 (dq, J=7.0, 1.0 Hz), 1.54 (dd, J=7.0, 1.0 Hz), 1.78 (s); showing that there are two tigloyl groups in its molecule. In the HMBC spectrum of compound 3, the following long-range correlations were observed: the carbonyl signal of the tigloyl group at $δ_C$ 167.8 was correlated with the signal of methine proton H-12 at $δ_H$ 5.26 (dd, J=11.0, 4.0 Hz) on an oxygen-bearing carbon (C-12) at $δ_C$ 74.7, and the carbonyl signal of another tigloyl group at $δ_C$ 166.6 was correlated with the signal of methine proton H-20 at $δ_H$ 5.04 (q, J=6.0 Hz) on an oxygen-bearing carbon (C-20) at $δ_C$ 73.7, establishing that the two tigloyl groups were located at hydroxyl groups of C-12 and C-20 of the steroid nucleus respectively. Thus, the structure of compound 3 was confirmed to be 12-O-tigloyl-20-O-tigloylsarcostin.

12-O-tigloyl-20-O-tigloylsarcostin, $C_{31}H_{46}O_8$, white amorphous powder, melting point, 136-138° C. EI-MS (positive): m/z 547.3 [M+H]$^+$. HR-EI-MS: 547.3273 ([$C_{31}H_{46}O_8$+H]$^+$; calc. 547.3271); 569.3088 ([$C_{31}H_{46}O_8$+Na]$^+$; calc. 569.3090). $^{13}$C NMR($C_5D_5N$, 125 MHz): 38.9 (C-1), 32.0 (C-2), 71.5 (C-3), 43.3 (C-4), 140.1 (C-5), 118.7 (C-6), 34.9 (C-7), 74.3 (C-8), 43.9 (C-9), 37.1 (C-10), 25.7 (C-11), 74.7 (C-12), 56.9 (C-13), 88.8 (C-14), 34.1 (C-15), 33.8 (C-16), 87.7 (C-17), 11.4 (C-18), 18.2 (C-19), 73.7 (C-20), 15.3 (C-21), 167.8 (C-1'), 130.6 (C-2'), 136.7 (C-3'), 14.2 (C-4'), 12.3 (C-5'), 166.6 (C-1"), 129.6 (C-2"), 135.9 (C-3"), 14.3 (C-4"), 12.1 (C-5"). $^1$H NMR ($C_5D_5N$, 500 MHz): δ 3.83 (1H, dq, 10.0, 5.0 Hz, H-3), 5.36 (1H, d, 4.5 Hz, H-6), 5.26 (1H, dd, 11.0, 4.0 Hz, H-12), 2.04 (3H, s, H-18), 1.35 (3H, s, H-19), 5.04 (1H, q, 6.0 Hz, H-20), 1.43 (3H, d, 6.0 Hz, H-21), 6.88 (1H, dq, 7.0, 1.0 Hz, H-3'), 1.65 (3H, dd, 7.0, 1.0 Hz, H-4'), 2.02 (3H, s, H-5'), 6.80 (1H, dq, 7.0, 1.0 Hz, H-3"), 1.54 (3H, dd, 7.0, 1.0 Hz, H-4"), 1.78 (3H, s, H-5").

Embodiment 14: Preparation and Structural Identification of 12-O—(N-methyl) Anthraniloyl Deacetylmetaplexigenin (23)

5 kg of dried stems of *Stephanotis mucronata* (Blanco) Merr. were ground, and percolated with a water solution of ethanol (water volume percentage: 5%), then the ethanol extract was obtained. The ethanol extract was extracted with ethyl acetate. The ethyl acetate extract was hydrolyzed with 0.2 N methanol solution of sulfuric acid at 70° C. for 5 hours, neutralized with sodium bicarbonate, and concentrated. The concentrate was extracted with ethyl acetate, and the extract was 192 g of total aglycone. 16.7 g of Fr1, 13.0 g of Fr2 and 14.5 g of Fr3 were obtained through silica gel column chromatography of 192 g of total aglycone with dichloromethane and dichloromethane-methanol systems by gradient elution. After Rp-18 column chromatography, 13 g of Fr2 was eluted with a methanol-water system (50%→60%), and identified with TLC. Identical portions were combined, and 116 mg of compound 23 was obtained through HPLC and Sephadex LH-20 column chromatography.

Compound 23 was obtained as white amorphous powder, and showed an intense blue fluorescence in methanol solution, indicating the presence of an (N-methyl) anthraninoyl group [Yoshikawa K, Okada Y, Kann Y, Arihara S. Steroidal glycosides from the fresh stems of *Stephanotis lutchuensis* var. *japonica* (Asclepiadaceae). Chemical structures of Stehpanosides A-J. *Chemical and Pharmaceutical Bulletin*, 1996, 44, 1790-1796.]. The $^{13}$C NMR and DEPT spectra (125 MHz, $C_5D_5N$) showed that compound 23 contains 29 carbon atoms, including 4 $CH_3$, 7 $CH_2$, 8 CH and 10 quaternary carbons. In comparison with metaplexigenin [Ye Y P, Li X Y, Sun H X, Chen F Y, Pan Y J Immunomodulating Steroidal Glycosides from the Roots of *Stephanotis mucronata*. Helvetica Chimica Acta 2004; 87:2378-2384.], compound 23 showed the absence of an acetyl group, but the existence of an (N-methyl) anthraninoyl group. Through the $^1$H signals at $\delta_H$ 6.66 (d, J=8.5 Hz), 7.42 (ddd, J=8.5, 8.0, 1.5 Hz), 6.73 (td, J=7.5, 1.5 Hz), 8.16 (dd, J=8.0, 1.5 Hz), 8.21 (q, J=5.0 Hz), 2.69 (d, J=5.0 Hz), and the $^{13}$C signals at $\delta_C$ 110.55 (s), 152.7 (s), 111.4 (d), 134.9 (d), 114.5 (d), 131.7 (d), 167.5 (s), 29.3 (q), the (N-methyl) anthraninoyl group was identified. In the HMBC spectrum of compound 23, the following long-range correlations were observed: the carbonyl signal at $\delta_C$ 167.5 was correlated with the signal of a methine proton (H-12) at $\delta_H$ 5.31 (dd, 11.5, 4.0), establishing that the (N-methyl) anthraninoyl group was at C-12. Thus, the structure of compound 23 could be established as 12-O—(N-methyl) anthraninoyl deacylmetaplexigenin.

12-O—(N-methyl) anthranilloyl deacetylmetaplexigenin, $C_{29}H_{39}NO_2$, white amorphous powder, melting point: 170-173° C. HR-ESI-MS: 514.2803 ($[C_{29}H_{39}NO_7+H]^+$; calcd. 514.2805); 536.2620 ($[C_{29}H_{39}NO_7+Na]^+$; calcd. 536.2624). $^{13}$C NMR ($C_5D_5N$, 125 M Hz): 39.1 (C-1), 32.0 (C-2), 71.5 (C-3), 43.3 (C-4), 140.3 (C-5), 118.4 (C-6), 34.7 (C-7), 74.3 (C-8), 44.4 (C-9), 37.3 (C-10), 25.1 (C-11), 73.1 (C-12), 58.3 (C-13), 92.4 (C-14), 33.8 (C-15), 33.2 (C-16), 89.6 (C-17), 10.9 (C-18), 18.3 (C-19), 209.9 (C-20), 27.7 (C-21), 110.55 (C-1'), 152.7 (C-2'), 111.4 (C-3'), 134.9 (C-4'), 114.5 (C-5'), 131.7 (C-6'), 167.5 (C-7'), 29.3 ($NCH_3$). $^1$H NMR ($C_5D_5N$, 500 MHz): δ 3.90 (1H, m, H-3), 5.33 (1H, d, 4.5 Hz, H-6), 5.31 (1H, dd, 11.5, 4.0 Hz, H-12), 2.07 (3H, s, H-18), 1.39 (3H, s, H-19), 2.39 (3H, s, H-21), 6.66 (1H, d, 8.5 Hz, H-3'), 7.42 (3H, ddd, 8.5, 8.0, 1.5 Hz, H-4'), 6.73 (3H, td, 7.5, 1.5 Hz, H-5'), 8.16 (1H, dd, 8.0, 1.5 Hz, H-6'), 2.69 (3H, d, 5.0 Hz, H—$NCH_3$), 8.21 (1H, q, 4.5 Hz, H—NH).

Embodiment 15: Preparation of Caudatin-3-Sulfate 4 mL of pyridine and 2.2 g (14 mmol) of sulfur trioxide-pyridine complex were added to 1.7 g (3.5 mmol) of caudatin under vacuum conditions under nitrogen protection while stirring at 70° C. for 4 h. Then concentrated to dry, and 20 mL of methanol and 10 g cationic resin were added, and stirred for 12 h. 2.9 g of yellow solid was obtained through filtration and concentration. After isolation and purification, the structure was determined by NMR and MS to be caudatin-3-sulfate with the following experimental data: $^{13}$C NMR ($C_5D_5N$, 125 MHz): 38.5 (C-1), 28.7 (C-2), 75.8 (C-3), 39.7 (C-4), 138.9 (C-5), 119.0 (C-6), 34.2 (C-7), 73.6 (C-8), 43.6 (C-9), 36.7 (C-10), 24.3 (C-11), 72.0 (C-12), 57.2 (C-13), 91.5 (C-14), 33.5 (C-15), 32.2 (C-16), 88.9 (C-17), 10.5 (C-18), 18.0 (C-19), 209.2 (C-20), 27.4 (C-21), 165.1 (C-1'), 113.6 (C-2'), 165.1 (C-3'), 37.6 (C-4'), 21.3 (C-5', 9'), 21.1 (C-6', 8'), 16.4 (C-7').

Embodiment 16: Preparation of Qingyangshengenin-3-Sulfate 2 mL of pyridine and 127 mg (0.8 mmol) of sulfur trioxide-pyridine complex were added to 200 mg (0.4 mmol) of qingyangshengenin under vacuum conditions under nitrogen protection while stirring at 70° C. for 4 h. Then concentrated to dry, and 10 mL of methanol and 5 g cationic resin were added, and stirred for 12 h. 213 mg of yellow liquid was obtained through filtration and concentration. After isolation and purification, the structure was determined by NMR and MS to be qingyangshengenin-3-sulfate with the following experimental data: HR-ESI-MS: 579.1906 ($[C_{28}H_{36}O_{11}S—H]^-$, calculated value: 579.1900). $^{13}$C NMR ($C_5D_5N$, 125 MHz): 38.9 (C-1), 29.0 (C-2), 78.2 (C-3), 40.0 (C-4), 139.2 (C-5), 119.5 (C-6), 34.8 (C-7), 74.4 (C-8), 44.5 (C-9), 37.2 (C-10), 25.1 (C-11), 73.4 (C-12), 58.4 (C-13), 89.5 (C-14), 33.2 (C-15), 33.9 (C-16), 92.5 (C-17), 10.8 (C-18), 18.1 (C-19), 209.7 (C-20), 27.7 (C-21), 165.4 (C-1'), 122.1 (C-2'), 132.4 (C-3'), 116.2 (C-4'), 163.6 (C-5').

Embodiment 17

Water for injection was conventionally added to sarcostin obtained through the method in Embodiment 1 to prepare an injection by refined filtration, encapsulation and sterilization.

Embodiment 18

Sarcostin obtained through the method in Embodiment 1 was dissolved in sterile water for injection while stirring, filtered with a sterile suction funnel, refined by sterile filtration, subpacked in ampoule bottles, hypothermally lyophilized and sterilely sealed to obtain a powder injection.

Embodiment 19

Sarcostin obtained through the method in Embodiment 1 was mixed with an excipient at a certain ratio to obtain a powder.

Embodiment 20

Sarcostin obtained through the method in Embodiment 1 was mixed with an excipient at a certain ratio, and then pelletized and tableted.

Embodiment 21

Sarcostin obtained through the method in Embodiment 1 was prepared into an oral solution using a conventional oral solution preparation method.

Embodiment 22

Sarcostin obtained through the method in Embodiment 1 was mixed with an excipient at a certain ratio to obtain a capsule or a granule or an electuary.

In order to better understand the advantages of the present invention, the pharmacological action of the compound sarcostin represented by the formula I in the present invention is described by an experimental example, which, however, is not intended to limit the present invention.

Experimental Example 1: Antidepressant Activity of Sarcostin

Experimental method: the experiment was made using the mouse forced swimming test and tail suspension test according to the experimental methodology of pharmacology (see the description of these methods in Xu Shuyun et al. *Experimental Methodology of Pharmacology*. People's Medical Publishing House, 2005: 807-808) by subacute treatment (administered twice within 24 hours) and by intraperitoneal administration. The solvent control and the positive control with fluoxetine and imipramine were established in the experiment.

Administration method: totally 6 dosage groups of sarcostin were established: 0.05, 0.1, 0.25, 0.5, 1, 5 mg/kg. Male Kunming mice were randomly grouped in the experiment. All test samples were intraperitoneally administered at a volumetric dose of 0.1 mL/10 g. Administration frequency and time: test was made twice respectively in 0 and 19 h, and test was made in 24 h after the first administration. Positive control: 15 mg/kg of fluoxetine and 15 mg/kg of imipramine.

Experimental results: compared with normal saline control, 15 mg/kg fluoxetine and 15 mg/kg imipramine significantly reduced the immobility time of mice in forced swimming test, and showed significant antidepressant activities; 0.05 to 0.5 mg/kg sarcostin also had significant antidepressant activities and significant dose-effect relationship, where the preferred dose was 0.1 mg/kg (see Table 2).

Experimental Example 2: Preliminary Acute Toxicity Test of Sarcostin

Experimental method: 20 clean male ICR mice were randomly divided into two groups, and fasted for 12 h before the experiment. Sarcostin was administered many times based on its maximum dissolution amount and maximum administration volume. For the oral administration group, sarcostin was prepared with ultra-pure water (maximum dissolution amount: 1.5 mg/mL), and was intragastrically administered four times in 24 hours with 0.3 ml/10 g body weight each time, and with the total dosage of 180 mg/kg. For the intraperitoneal injection group, sarcostin was prepared with normal saline (maximum dissolution amount: 1.0 mg/mL), and was intraperitoneally injected four times in 24 hours with 0.3 ml/10 g body weight each time, and with the total dosage of 120 mg/kg. After administration of drugs, the toxic reaction of mice was observed for 7 consecutive days.

Experimental results: under the maximum dissolution amount and the maximum administration volume, 180 mg/kg sarcostin was intragastrically administered, and 120 mg/kg sarcostin was intraperitoneally injected, but all mice were in good conditions with steady weight gain and without obvious toxic and side reaction.

TABLE 2

Effect of Sarcostin in Mouse Forced Swimming Test

| | Dosage group (mg/kg) | Male (/) | Immobility time (Average value, s) | Standard deviation | Standard error | P |
|---|---|---|---|---|---|---|
| Normal Saline | 0.1 ml/10 g | 20 | 146.40 | 45.49 | 10.17 | |
| Fluoxetine | 15 | 8 | 79.00 | 25.27 | 8.93 | *<0.001 |
| Imipramine | 15 | 20 | 92.05 | 41.87 | 9.36 | *<0.001 |
| Sarcostin | 0.05 | 8 | 85.13 | 34.69 | 12.27 | *<0.001 |
| | 0.1 | 8 | 83.63 | 18.85 | 6.67 | *<0.001 |
| | 0.25 | 8 | 112.63 | 23.87 | 8.44 | 0.041 |
| | 0.5 | 16 | 118.19 | 45.05 | 11.26 | 0.033 |
| | 1 | 16 | 125.44 | 44.20 | 11.05 | 0.112 |
| | 5 | 8 | 91.50 | 26.93 | 9.52 | 0.001 |

Note:
*means significant statistical difference, compared with the normal saline group.

Compared with the normal saline group, fluoxetine and imipramine significantly reduced the immobility time of mice in tail suspension test, while sarcostin did not significantly reduce the immobility time of mice in tail suspension test, but 0.1, 0.5 and 0.05 mg/kg groups showed antidepressant trend, and 0.5 mg/kg was the preferred dosage (see Table 3).

In Table 1, the antidepressant compound 3, antidepressant compound 23 and their derivatives with $R_1$ group being sulfate or acetate, were also assayed by the antidepressant activity test and preliminary acute toxicity test showing that these compounds have significant antidepressant activities, and have no significant toxic and side reaction.

TABLE 3

Effect of Sarcostin in Mouse Tail Suspension Test

| | Dosage group (mg/kg) | Male (/) | Immobility time (Average value, s) | Standard deviation | Standard error | P |
|---|---|---|---|---|---|---|
| Normal Saline | 0.1 ml/10 g | 16 | 206.68 | 53.78 | 13.44 | |
| Fluoxetine | 15 | 16 | 132.45 | 61.10 | 15.27 | *0.001 |
| Imipramine | 15 | 16 | 155.37 | 64.98 | 16.24 | *0.020 |
| Sarcostin | 0.05 | 16 | 177.94 | 56.69 | 14.17 | 0.188 |
| | 0.1 | 16 | 167.77 | 57.46 | 14.36 | 0.076 |
| | 0.25 | 16 | 207.60 | 74.39 | 18.60 | 0.966 |
| | 0.5 | 16 | 166.46 | 74.12 | 18.53 | 0.066 |
| | 1 | 16 | 200.99 | 45.12 | 11.28 | 0.794 |
| | 5 | 16 | 177.05 | 59.95 | 14.99 | 0.175 |

Note:
*means significant statistical difference, compared with the normal saline group.

What is claimed is:

1. A method of treating depression comprising:
administering an antidepressant compound to a patient in need thereof, the antidepressant compound represented by formula I:

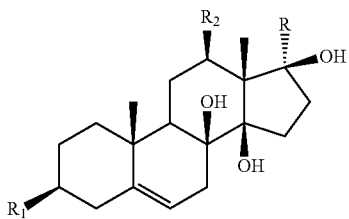

Formula I wherein a substituent $R_1$ is a hydroxyl group;
a substituent $R_2$ is a hydroxyl group; and
a substituent R is an acetyl group or $CH_3CHR_3$, wherein a substituent $R_3$ in $CH_3CHR_3$ is a hydroxyl group.

2. A method of treating depression comprising:
administering an antidepressant composition to a patient in need thereof, the antidepressant composition comprising the antidepressant compound represented by formula I in claim 1.

3. The method of treating depression of claim 2, wherein the antidepressant compound serves as the only active ingredient or one of a plurality of active ingredients of the antidepressant composition.

4. The method of treating depression according to claim 2, wherein the antidepressant composition is a liquid preparation, a solid preparation, a spray or an aerosol.

5. The method of treating depression according to claim 4, wherein the liquid preparation is an injection, a suspension, an emulsion, a solution or a syrup.

6. The method of treating depression according to claim 4, wherein the solid preparation is a tablet, a capsule, a granula or an electuary.

* * * * *